US006563580B1

(12) United States Patent
Aignel et al.

(10) Patent No.: US 6,563,580 B1
(45) Date of Patent: May 13, 2003

(54) METHOD AND DEVICE FOR DETERMINING MEAT TENDERNESS

(75) Inventors: Denis Aignel, Cesson-Sevigne (FR); Patrick Faure, Saint-Gregoire (FR); Patrice Laumonier, Balaze (FR)

(73) Assignee: Societe Vitreenne d'Abattage, Vitre (FR)

(*) Notice: Subject to any disclaimer, the term of this patent is extended or adjusted under 35 U.S.C. 154(b) by 0 days.

(21) Appl. No.: 09/743,022

(22) PCT Filed: Jun. 14, 1999

(86) PCT No.: PCT/FR99/01404

§ 371 (c)(1),
(2), (4) Date: Jan. 3, 2001

(87) PCT Pub. No.: WO00/02043

PCT Pub. Date: Jan. 13, 2000

(30) Foreign Application Priority Data

Jul. 3, 1998 (FR) ............................................. 98 08536

(51) Int. Cl.⁷ ............................. G01J 3/00; G01N 33/12
(52) U.S. Cl. ........................................ 356/300; 250/910
(58) Field of Search ........................... 356/300; 250/910

(56) References Cited

U.S. PATENT DOCUMENTS

| 3,493,774 A | | 2/1970 | Knudsen .................... 250/226 |
| 4,009,390 A | * | 2/1977 | Satterlee et al. ............... 378/45 |
| 5,088,822 A | * | 2/1992 | Kanda ......................... 356/326 |
| 6,198,834 B1 | * | 3/2001 | Belk et al. ..................... 348/89 |

FOREIGN PATENT DOCUMENTS

| EP | 0 402 877 | 12/1990 |
| EP | 0 444 675 | 9/1991 |
| FR | 1 550 169 | 12/1968 |
| WO | WO 94/00997 | 1/1994 |
| WO | WO 98/20339 | 5/1998 |

OTHER PUBLICATIONS

Research Guidelines for Cookery, Sensory Evaluation and Instrumental Tenderness Measurements of Fresh Meat, 1995, pp. 1–49, American Meat Science Association, Chicago, Illinois.

Wheeler, T.L. et al., Effects of Cooking and Shearing Methodology on Variation in Warner–Bratzler Shear Force Values in Beef, Journal of Animal Science, 1994, pp. 2325–2330.

Naes, et al., "Comparison of Multivariate Calibration and Discriminant Analysis In Evaluating NIR Spectroscopy for Determination of Meat Tenderness," Applied Spectroscopy, vol. 51, No. 3, Mar. 1997, pp 350–357.

Chen, et al., "Transportable Spectrophotometer System for On–line Classification of Poultry Carcasses," Applied Spectroscopy, vol. 50, No. 7, Jul. 1996, pp 910–916.

* cited by examiner

Primary Examiner—F. L. Evans
Assistant Examiner—Kara Geisel
(74) Attorney, Agent, or Firm—Christie, Parker & Hale, LLP

(57) ABSTRACT

The invention concerns a method for determining the quality of meat, in particular beef, on the transformation site, comprising the following steps: a) collecting, on the transformation site, data on parameters pertaining to the group consisting of the animal's race, age, and category, and biological and/or physico-chemical parameters of the animal's carcass pertaining to the group consisting of weight, conformation, fleshing, the carcass pH and color, and the thickness of the hide; b) obtaining at least an optical spectrum of the meat at wavelengths pertaining to a spectral range from the visible to near-infrared; c) combining data obtained from steps a) and b), to determine the meat tenderness according to a predetermined law established with respect to a predetermined tenderness reference scale.

15 Claims, 4 Drawing Sheets

METHOD AND DEVICE FOR DETERMINING MEAT TENDERNESS

CROSS REFERENCE TO RELATED APPLICATIONS

This application claims priority of International application No. PCT/FR99/01404, dated Jun. 14, 1999, which in turn claims priority of French application No. 98/08536, filed Jul. 3, 1998.

The present invention relates to the determining of the tenderness of meat, in particular of beef, on the transformation site by means of biological and/or physico-chemical data and optical measurements in the visible and near infrared range.

Among the numerous factors of quality of meat, such as juiciness, tenderness, colour, or flavour, tenderness is considered as the factor of quality which gives the most satisfaction to the consumer.

It is therefore economically important for meat producers to be able to determine the tenderness of a meat rapidly and as early as possible in the process of transforming the meat in the industrial environment (abattoir). Moreover, and above all, this determination must be reliable in order to guarantee the quality up to the stage of consumption.

A large number of industrial methods of determining the quality of meat are already known, in particular of the non-destructive type (i.e. without cutting away samples).

In the French Patent 1 550 169, a probe determines the colours of meat by means of a light transmitted by a piece of meat subjected to observation. The instrument comprises an emission branch and a reception branch intended to be inserted into the meat. A lamp gives out a light by the emission branch located opposite the reception branch. Such a document does not specify the wavelengths of the light used. Moreover, only the colours of the meat are determined, which is insufficient in order to determine the tenderness of the meat with a satisfactory degree of reliability.

In the publication EP-A-0402877, a probe is inserted into a piece of meat in order to determine its quality. The technique used is to measure the intensity of light reflected (reflectance) in the visible or near infrared spectrum. With such a probe it is only possible to estimate the concentrations of one or more components of the meat, which is not sufficient to determine the tenderness of the meat with a satisfactory degree of reliability.

The object of the present invention is to improve the reliability of the prior techniques for determining the quality and in particular to determine the tenderness on the transformation site.

The invention relates to a method of determining the quality of meat, in particular beef, which can be used on a production line on the transformation site.

According to a general definition of the invention, the method comprises the following stages:

a) to collect, on the transformation site, data relating to parameters belonging to the group formed by the breed, age and category of animal as well as biological and/or physico-chemical parameters of the animal carcass belonging to the group formed by the weight, conformation, fleshing, the pH value and the colour of the carcass, as well as the thickness of the hide, b) to obtain at least one optical spectrum of the meat corresponding to wavelengths belonging to a spectral field ranging from visible light to near infrared, and c) to combine the data obtained at stages a) and b) with a view to determining the tenderness of the meat according to a predetermined equation drawn up relative to a predetermined scale of reference of tenderness.

The Applicants have observed that certain parameters of the animal and its carcass, such as breed, age and type of animal as well as weight, conformation, fleshing, the pH value, the colour of the carcass and the thickness of the hide etc. are data which are correlated with tenderness.

However, until now no model for determining tenderness has used these data directly, probably due to ignorance or a lack of interest therein on the part of scientists.

In spite of this prejudice, the Applicants use them in order to combine them furthermore with optical measurements with a view to a more reliable determination of the tenderness of meat on the transformation site.

The data (breed, age, category of animal, weight, conformation, fleshing, pH value, carcass colour, thickness of hide etc.) are hereinafter referred to as "expert data", because they derive from an in-depth knowledge of the animal and the features which influence tenderness.

The method according to the invention makes it possible to supply an objective, nondestructive determination of the tenderness of meat which can be carried out on a production line on the transformation site in an industrial environment without having recourse to sophisticated, expensive devices.

Moreover, the results of determination according to the invention are sufficiently reliable to be able to guarantee tenderness with a high level of probability at the time when the meat leaves the transformation site in an industrial environment.

In practice, the stage b) is effected in reflection and/or emission mode.

In transmission mode, stage b) comprises the following stages:

b 1) to provide a probe comprising an emission branch and a reception branch, spaced apart by a predetermined distance;

b 2) to insert the emission and reception branches into a selected piece of meat to a selected depth;

b 3) to illuminate the piece of meat by means of the emission branch thus inserted into the piece of meat by wide-band light radiation at a frequency ranging from visible light to near infrared;

b 4) to receive the light transmitted by the piece of meat by means of the receiving branch thus inserted into the piece of meat; and b 5) to record a transmission spectrum of the piece of meat ranging from visible light to at least near infrared.

In reflection mode, the probe comprises a single branch for emission and reception of the incident light and reflected light respectively.

In practice, the determination equation is drawn up over a significant series of different pieces of meat of different animals for each of which spectral data and non-spectral data are obtained according to stages a) and b) and compared to a scale of reference drawn up by means of sensorial data and/or data of the shearing force, and/or of the force of compression measured over the significant series of different pieces of meat.

Preferably, determination is carried out by a multidimensional statistical method such as the method of smallest partial squares, in order to obtain a mathematical determination model intended to be used on each piece of meat whose tenderness is to be determined.

According to another feature of the method, stage b) is effected on the carcass, quarters, muscles or steaks.

A further object of the present invention is a device for determining the quality of meat, in particular beef, on the transformation site.

According to a general definition of the device according to the invention, the device comprises:

- means of collecting on the transformation site data relating to parameters belonging to the group formed by the breed, age and category of animal as well as biological and/or physicochemical parameters of the animal carcass belonging to the group formed by the weight, conformation, fleshing, the pH value and the colour of the carcass, as well as the thickness of the hide,
- means of obtaining at least one optical spectrum of the meat corresponding to wavelengths belonging to a spectral field ranging from visible light to near infrared, and
- processing means for combining the data obtained at stages a) and b) with a view to determining the tenderness of the meat according to a predetermined equation relative to a predetermined scale of reference of tenderness.

Further features and advantages of the invention will appear from the detailed description below and from the attached drawings, in which.

The drawings comprise in essence elements of a certain character. To this end, they may not only help to explain the detailed description below, but also contribute, if necessary, to the definition of the invention.

The present invention is intended more particularly to be put into effect on a meat transformation site (slaughter and cutting up), e.g. on the continuous production line of an industrial abattoir.

It is applied to any type of meat, in particular originating from cows, sheep, goats, pigs or the like.

In general, a slaughter and cutting site comprises a reception bay for live animals, a slaughter bay, bays for preparation of the slaughtered animals to form carcasses, bays for cutting at least into demi-carcasses, a phase of bleeding, and if necessary bays for cutting and preparation into quarters, muscles or steaks.

Certain features or parameters of the animal and its carcass are known or easily measurable on the transformation site.

For example, the breed RA (Charolais, Limousine etc.), age AG, category CA (young cow, ox, cow, heifer etc.) of animal are gathered at the bay for receiving the live animal. These data, together with the origin of the animal NE, are available on the animal's identity card.

Figure 1:
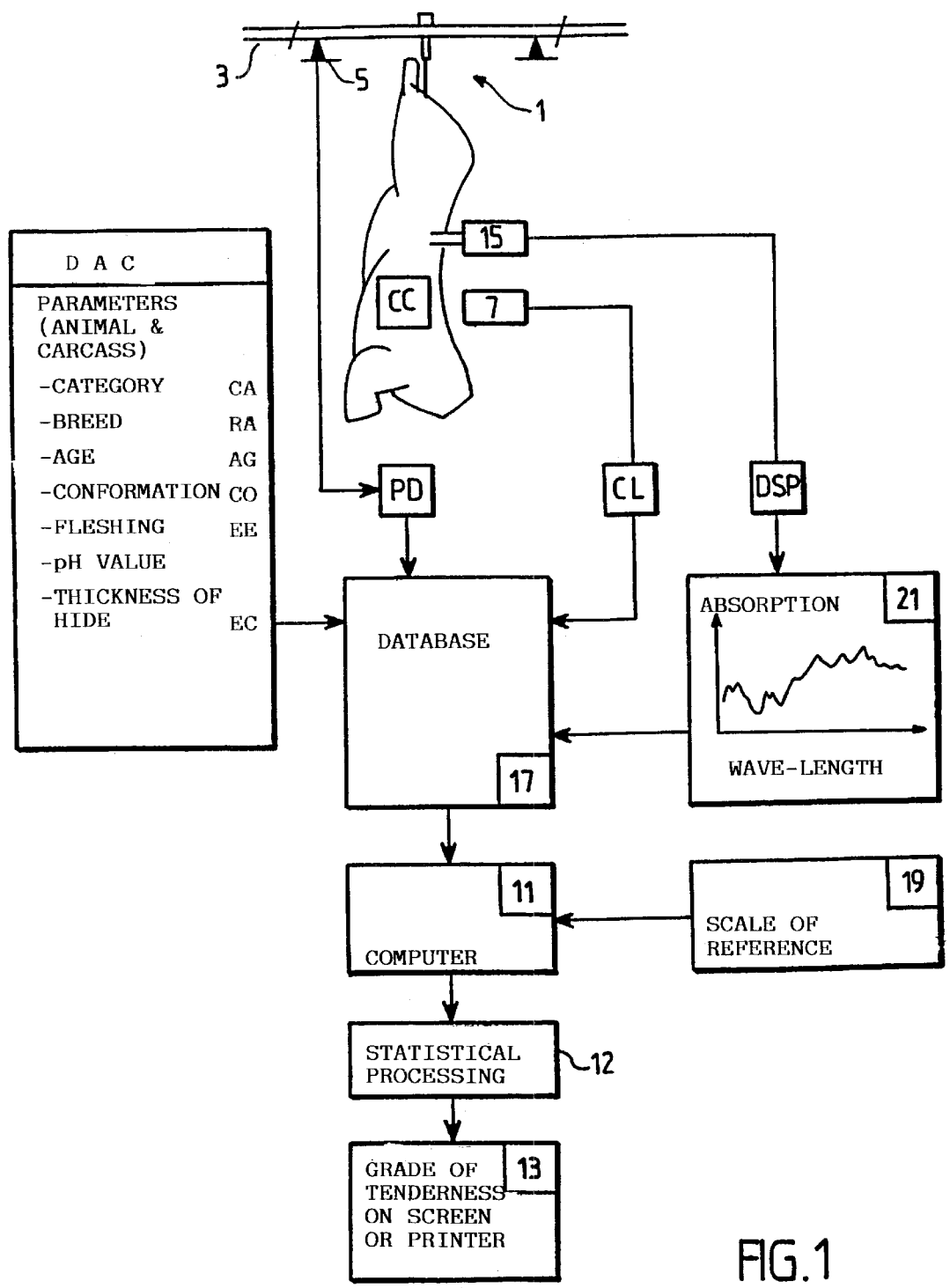
FIG. 1 shows diagrammatically a continuous production line of an industrial abattoir on which the invention is set up.

With reference to FIG. 1, biological and/or physico-chemical features or parameters of the animal are measured on the transformation site, in particular on the continuous production line 1 of an industrial abattoir.

Among these features is found the weight PD of the carcass, which is measured by means of a weighing scale 5 placed on the aerial conveyor 3 of the continuous production line 1, e.g. before the bleeding bay.

The conformation CO of the carcass CC is also evaluated. Five levels of conformation CO are provided in accordance with the EUROP classification grid, whose criteria are in particular described in regulation no. 1208/81 of the Council of European Communities of Apr. 28, 1981, which lays down the community classification grid for beef carcasses as well as in regulation no. 1026/91 of the Council of European Communities of Apr. 22, 1991.

The fleshing EE of the carcass CC is also evaluated. Five levels vary between "very poor" and "very good". In practice, the fleshing EE is evaluated before the bleeding bay according to criteria described in particular in regulation no. 1208/81 of the Council of European Communities of Apr. 28, 1981 mentioned above.

The colour CL of the carcass CC is likewise measured, e.g. before the bleeding bay. Measurement of the colour CL may be obtained by a colorimeter 7. An expert may also measure the colour CL of the carcass CC with the naked eye.

The pH value (degree of acidity) of the carcass CC may also be measured by means of an instrument for measuring acidity (not shown) at various times after slaughter, e.g. 1, 2, 3, 8, 12 or 24 hours after slaughter. For example, the pH value of the carcass is measured according to the French standard NF V 46-001 of December 1996 entitled "Viandes de gros bovins-conditions de valorisation du potentiel de tendreté" (Meat from full-grown beef cattle-conditions for evaluating the potential for tenderness).

Another relevant indicator for determining tenderness, as will be seen in more detail below, is the thickness of the hide EC, which may be measured after slaughter by means of weighing the hide combined with, or not, measurement of the surface area thereof.

All these data DAC, known as expert data, are recorded and stored in a computer memory 11 connected to a printer and a monitor 13.

The Applicants have observed that it may be advantageous to integrate these expert data DAC into a model for determining tenderness.

Moreover, the results of determination are further improved when these expert data DAC are combined with optical spectral data DSP relating to the reflection and/or emission of the meat within the visible and near infrared range.

It should be noted that in the presence of animals having substantially the same biological and/or physico-chemical characteristics DAC, determination of tenderness may be effected, with a relatively satisfactory degree of reliability, only on the basis of optical measurements ranging from visible light to near infrared.

Furthermore, in the case of animals having different biological and/or physico-chemical characteristics, the number of biological and/or physico-chemical characteristics to be combined depends on the degree of reliability of determination of tenderness to be reached.

Thus, the degree of reliability of determination which integrates numerous DAC parameters will be better than that of a determination which only integrates a few DAC parameters.

The spectral measurements DSP may be obtained on the transformation site before, during or after bleeding, and on carcass, quarters, muscles or steaks by means of a suitable apparatus 15.

The computer 11 is capable of determining the tenderness of the piece of meat thus observed according to a predetermined equation of determination of tenderness in order to attach or print the level of tenderness of the piece of meat on a suitable band 13.

In practice, the equation for determination is drawn up over a significant series of different pieces of meat (sirloin, topside etc.) of different animals (cows, young beef cattle, etc.) for each of which spectral data DSP and non-spectral data DAC are obtained and compared to a selected scale of reference 19.

The spectral data DSP are obtained by means of at least one optical measurement of the light transmitted and/or reflected by the piece of meat in transmission and/or reflection mode, which will be described in more detail with an example. The optical measurement is advantageously carried out in the range of 400–2500 nm, if necessary restricted to 400–2100 nn.

The spectral data DSP of various pieces of meat from different animals are stored in a memory 21 in association with the non-spectral data DAC of each animal. All these data DAC and DSP are managed in a database 17.

For each cow (or other animal), data DAC are available from the database 17. The spectral data DSP and non-spectral data DAC thus obtained are compared to a selected scale of reference 19.

For example, the scale of reference 19 is drawn up by means of sensorial data and/or data of shearing force and/or compression force obtained on each piece of meat of each animal taking part in drawing up the equation of determination.

The reference data of tenderness 19 are stored in the database 17 connected to the computer 11.

The shearing forces are established for example according to a method of the WARNER BRATZLER type, defined by WHEELER, KOOHMARAIE, CUNDIF and DIKE in 1994 in their study entitled "Effects of cooking and shearing methodology on variation in Warner Bratzler shear force values in beef", which appeared in the periodical "Journal of Animal Science", no. 72, 1994.

As a variant, the compression force is established on slices of steak boiled according to the VOLODKEWICH method.

The scale of reference 19 may be evaluated also by means of a tasting jury, as is described in "Research Guidelines for Cookery, Sensory Evaluation and Instrumental Tenderness Measurements of Fresh Meat", published by the American Meat Science Association, 1995 edition.

In the case of sirloins of beef, the tenderness of each of these is evaluated for example by a measurement of the shearing force according to the Warner Bratzler method mentioned above.

An analysis is then carried out on each optical spectrum according to a selected statistical processing method 12, e.g. an "analysis of main components known as AMC". This AMC makes it possible for example to isolate the first 10 main components which will form the spectral variables DSP of the spectral model according to the invention.

In practice, each parameter (spectral data DSP or expert data DAC) is considered an individual variable used in a mathematical model 12 (e.g. multiple regression) in order to determine tenderness.

The equation or model of determination may be of the type:

$$\text{Determination of tenderness} = C + a_1 X_1 + a_2 X_2 + \ldots + a_n X_n$$

where

C is a constant $a_1$ to $a_n$ are coefficients, and $X_1$ to $X_n$ are the spectral variables DSP and non-spectral variables DAC.

An experiment was carried out on 100 sirloins of beef The mathematical model, taking into account the entire spectrum from 400 to 2500 nm in reflection mode and the data DAC, makes it possible to determine tenderness with a coefficient of multiple correlation $R^2$ of 0.62.

More reliable models of determination were established on sub-populations of this sample. For example, for the 25 cows of the breeds Charolais, Limousine or a cross the determination of tenderness is associated with a coefficient of correlation $R^2$ of 0.95. This coefficient operates, in order of importance for the non-spectral variables DAC, the following parameters:

colour of the sirloin CL, thickness of hide EC, weight of carcass PD, conformation CO, pH value during bleeding, age of animal AG.

For the spectral data, the main components 3, 7, 11, 5, 10 and 2 are the most significant. They comprise the wavelengths generally used for detecting proteins, fat, water content, collagen, as well as the pigment of the meat. For example, these are the following wavelengths: 460, 660, 800, 880, 980, 1020, 1120, 1320, 1580, and 1920 nm.

Each of these parameters is correlated significantly with tenderness. However, taken alone, they do not guarantee tenderness with great probability. Thus, for example the colour of the sirloin is correlated with tenderness with a coefficient of correlation $R^2$ of 0.65, whereas the thickness of the hide is correlated with tenderness with a coefficient of 0.43.

In another example of the invention, the Applicants demonstrated that the spectral data DSP in emission mode make it possible to obtain a good determination of tenderness ($R^2$ of 0.6) on the topsides of 100 young cattle. This coefficient is improved by integrating certain expert data DAC. For example, a coefficient of correlation of 0.95 was obtained for topsides (semitendinosus) of 24 young cattle of milk-producing breed.

This coefficient brings into play, in order of importance for non-spectral variables, the following parameters:

pH value during bleeding, colour of the carcass CL, fleshing EE, thickness of hide EC, weight of carcass PD, age of animal AG.

In this example in transmission mode, certain preponderant wavelengths correspond to wavelengths generally used for determining the pigment of the meat (560 nm), fat (930 and 1215 nm) and water content (1682 nm).

Figure 2:
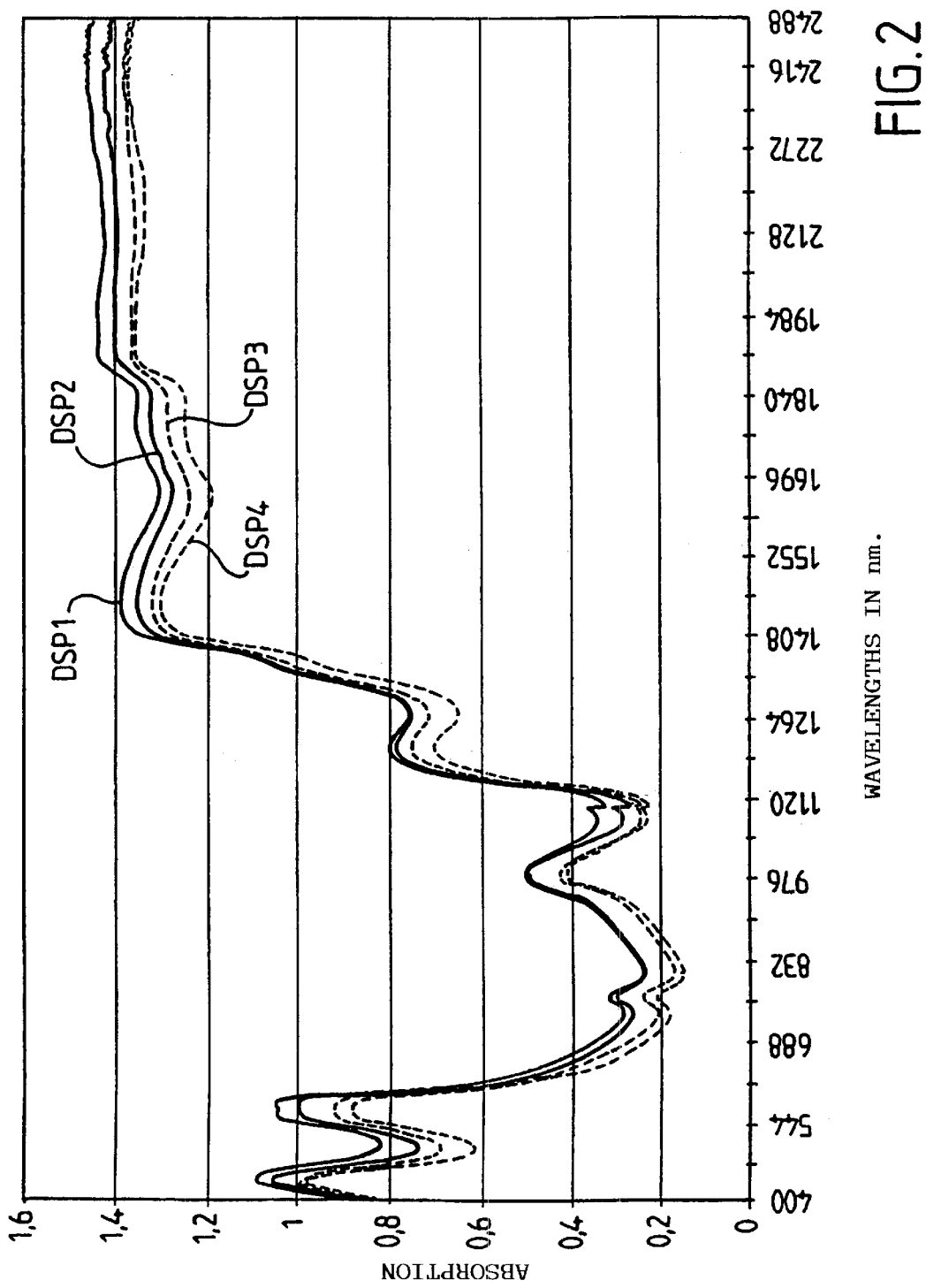
FIG. 2 shows spectra from absorption to reflection obtained on cows of different tenderness according to the invention.

With reference to FIG. 2, various absorption spectra are shown of sirloins of tough and tender cows from the visible (400 nm) to near infrared (2480 nm) in reflection mode.

It will be seen that certain peaks of absorption are strongly correlated with tenderness. It should be noted that it is desirable in terms of reliability to measure a full optical spectrum at least from 400 to 2100 nm.

The spectrum DSP1 is that of a sirloin of a cow whose tenderness is evaluated at 6.10 on the WARNER BRATZLER-type scale of reference, i.e. a tough sirloin.

The spectrum DSP2 is that of a sirloin of a cow whose tenderness is evaluated at 6.90 on the WARNER BRATZLER-type scale of reference, i.e. a tough sirloin.

The spectrum DSP3 is that of a sirloin of a cow whose tenderness is evaluated at 2.9 on the WARNER BRATZLER-type scale of reference, i.e. a tender sirloin.

The spectrum DSP4 is that of a sirloin of a cow whose tenderness is evaluated at 3.30 on the WARNER BRATZLER-type scale of reference, i.e. a tender sirloin.

Figure 3:
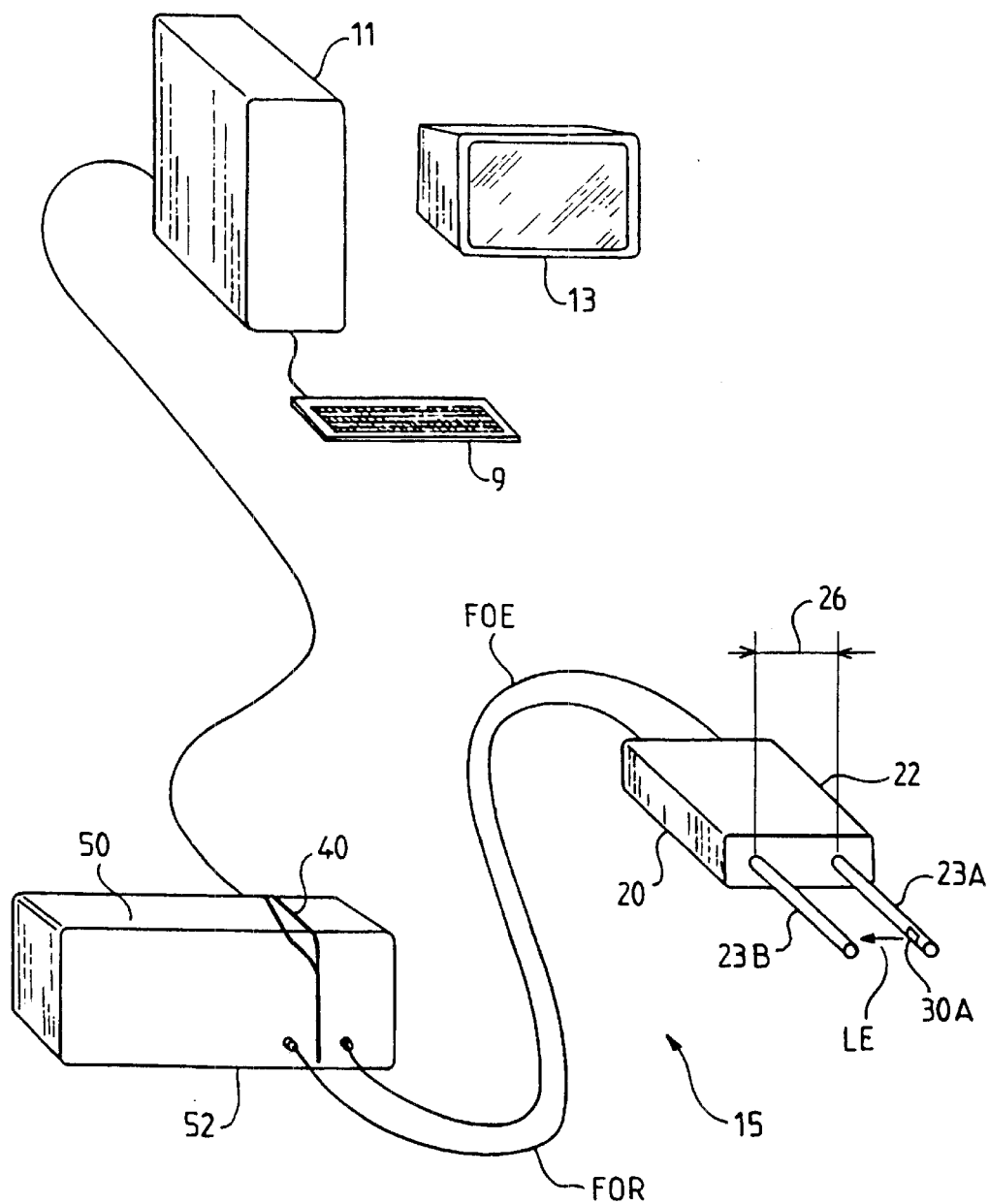
FIG. 3 shows diagrammatically the essential constituent means of a device for obtaining a transmission spectrum according to the invention.
Figure 4:
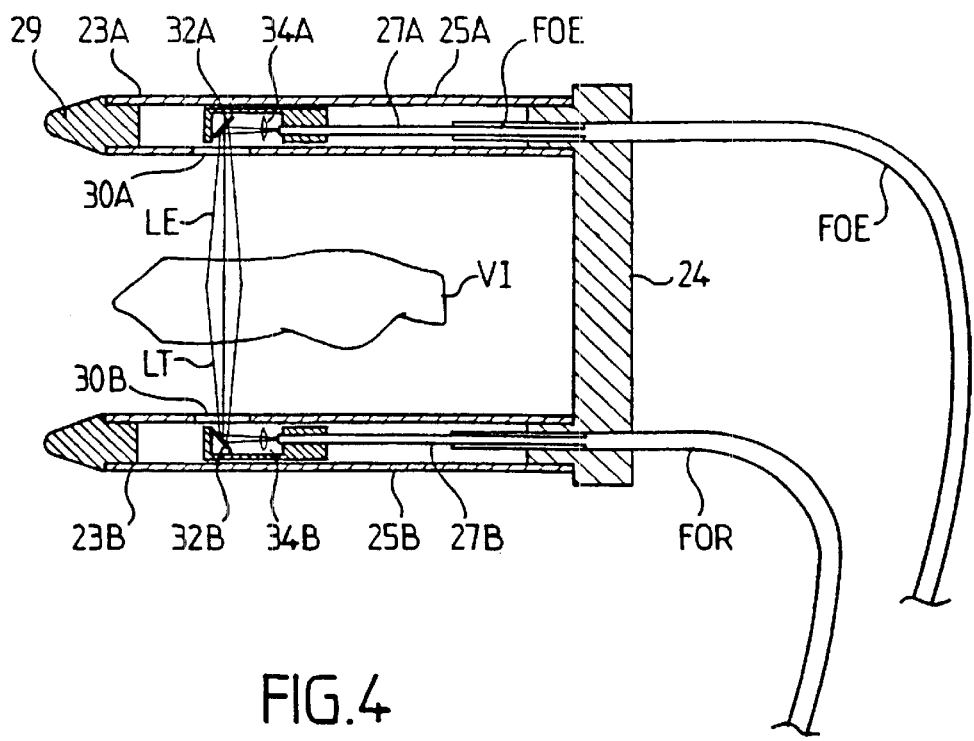
FIG. 4 is a section view showing a transmission probe according to the invention.

With reference to FIGS. 3 and 4, a device has been described for obtaining spectral data, operating in transmission mode.

The device for obtaining spectral data 15 comprises for example a gun-type pricking device 20 comprising a housing 22 and a probe 23 with two branches 23A and 23B, one 23A being dedicated for emission and the other 23B for reception. The branches 23A and 23B of the probe are intended to be inserted into a selected piece of meat to a selected depth. The branches 23A and 23B are parallel to one another and spaced apart at a predetermined distance. The two branches are connected together by a base 24 forming a support and rigid with the housing 22. The base 24 also acts as an interface for the optic fibres which will be described in more detail below.

Advantageously, the centre-distance of the axes 26 between the two branches 23A and 23B is adjustable between a minimum distance of 10 mm and a maximum distance of 40 mm.

It should be noted that the centre-distance 26 between the two branches is adjustable but always fixed during measuring. The depth of penetration of the probe may be adjusted between 5 and 15 cm The diameter of the penetrating branches is about 1 cm.

Advantageously the penetrating ends of the branches are equipped with stainless steel bungs 29.

The length of the branches 23A and 23B is 20 cm.

The branch 23A comprises a window 30A disposed on the inner side of its penetrating end, perpendicular to the axis of penetration, whereas the branch 23B comprises a window 30B disposed on the inner side of its penetrating end, perpendicular to the axis of penetration, and opposite the window 30A.

Each branch comprises a tube, referenced 25A for branch 23A and 25B for branch 23B. The tubes are hollow, e.g. made of silica.

The light radiation LE is emitted by a distant light source 40.

The light radiation LE is directed to the non-penetrating end of the branch 23A by a sheathed optic fibre FOE. In the tube 25A, the light radiation LE is first guided via an optic fibre 27A and then directed into a free space up to the window 30A. Finally, the light radiation LE is guided in free space from the window 30A to the piece of meat VI.

The light radiation LE illuminates the meat VI at 90° relative to the longitudinal axis of penetration of the branch 23A.

The diameter of the emitted light radiation LE is a few mm through the window 30A, which is for example made of quartz 1 to 2 mm thick.

A mirror 32A is placed between the outlet of the fibre 27A and the window 30A. The mirror 32A is oriented at 45° to the longitudinal axis of penetration of the emission branch 23A in order to reflect at 90° the light emanating from the optic fibre 27A.

An adapting optic 34A, of the lens type for example, is located between the outlet of the emitting optic fibre 27A and the mirror 30A in order to adapt the emitted light radiation LE to the volume of meat to be observed.

The light LT transmitted by the piece of meat VI is received in free space by the window 30B, disposed perpendicular to the axis of penetration of the reception branch 23B.

The diameter of the transmitted light radiation LT is a few mm. The reception of the light radiation transmitted LT is effected through a quartz window 30B 1 to 2 mm thick.

A mirror 32B is oriented at 45° to the longitudinal axis of penetration of the reception branch 23B in order to reflect the light transmitted LT towards a receiving optic fibre 27B disposed parallel to the longitudinal axis of penetration of the branch 23B.

An adapting optic 34B, of the lens type for example, is provided between the mirror 32B and the inlet of the optic fibre 27B in order to adapt the light radiation transmitted to the aperture of the optic fibre 27B.

The light transmitted LT is then directed towards measuring means 50 via a sheathed optic fibre FOR.

Preferably, the measuring means 50 comprise a spectrophotometer SPH equipped with a network (not shown) which disperses the light in different wavelengths ranging from the visible to near infrared. The light diffracted by the network hits a detection bar such as photodiodes each capable of recording the light-intensity transmitted in a selected range of wavelengths.

For example, the detection bar comprises silicon detectors for wavelengths smaller than 1050 nm and germanium detectors for lengths larger than 1050 nm.

An amplifying block (not shown) is provided after the detection block in order to achieve a signal level of between 1 and 10 volts, for example.

As an example, the light source 40 is a tungsten halogen lamp with a power of 20 to 40 Watts. The special features of such a lamp is to be able to emit, within a wide frequency band, a light radiation ranging for example from the visible spectrum to near infrared.

The probe 23 can be used manually. In this case, it may be separate from the light source 40 and the measuring means 50.

Advantageously, the light source and the measuring means are assembled in a common block 52, which is connected to a computer 11.

The optic fibres FOE and FOR have a length of 1 to 2 m in order to minimise attenuation. The diameters of the optic fibres are a few mm.

The emission of the light LE is advantageous interrupted by a rotating disc (not shown) located on the optical emission path, rotating for example at the frequency of 20 to 60 Hertz, in order to permit measurements of the signal transmitted in the absence or in the presence of emitted light.

This timed obstruction makes it possible to overcome variations in external light.

It should be noted that the device according to the invention can be formed as a housing comprising a lamp 40 and measuring means 50 incorporated in the probe 23 in a single portable housing.

The spectral measurements can also be obtained in reflection mode, with the application of a probe to the surface or penetration into the meat whose tenderness is to be determined.

A probe operating by reflection is simpler than a probe operating by transmission.

Figure 5:
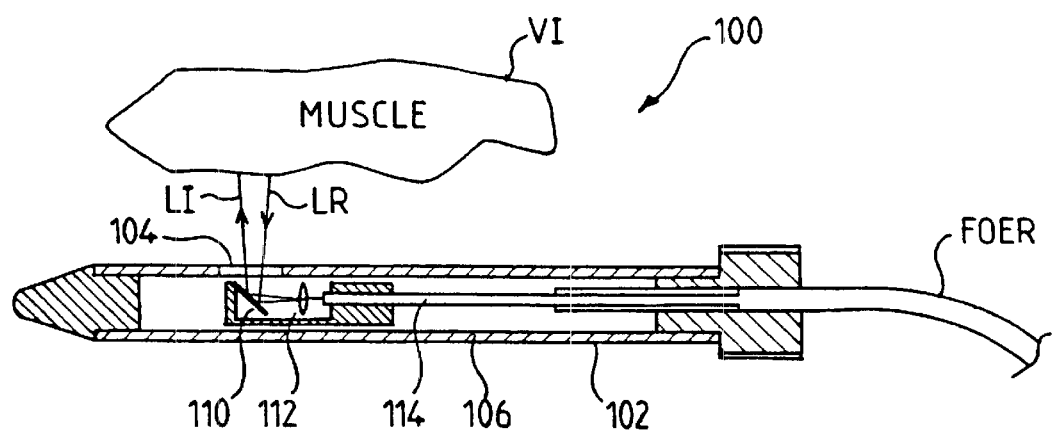
FIG. 5 is a section view showing the constituent means of a reflection probe according to the invention.

For example, with reference to FIG. 5, the probe 100 generally comprises a single branch 102 for carrying out the outward and return journey of the incident light LI and of the reflected light LR.

The branch 102 comprises a single window 104 disposed on the inner side of its penetrating end, perpendicular to the axis of penetration.

The branch comprises a tube 106, similar to those described with reference to FIG. 4.

The light radiation LI is emitted by a light source. The light radiation LI is directed to the non-penetrating end of the branch 102 by a sheathed optic fibre FOER. In the tube 106, the light radiation LI is first guided through an optic fibre 114 and then directed in free space to a window 104. Finally, the light radiation LI is guided in free space from the window 104 to the piece of meat VI.

The light radiation LI illuminates the meat VI at 90° to the longitudinal axis of penetration of the branch.

The diameter of the light radiation emitted LI is a few millimetres through the window 104, which is for example made of quartz 1 to 2 mm thick.

A mirror 110 is placed between the outlet of the fibre 114 and the window 104. The mirror 104 is oriented at 45° to the longitudinal axis of penetration of the branch 102 in order to reflect at 90° the light emanating from the optic fibre 114.

An adaptation optic 112, of the lens type for example, is placed between the outlet of the optic fibre 114 and the mirror 110 in order to adapt the light radiation emitted LI to the volume of meat to be observed.

The light reflected LR by the piece of meat VI is received in free space by the window 104 and crosses the branch in the opposite direction to that of propagation of incident light LI. The reflected light LR is then directed towards the measuring means by the emission/reception optic fibre FOER.

Like the probe described with reference to FIGS. 3 and 4, the probe 100 is connected to a light source and a spectrophotometer which may be similar to those described with reference to FIGS. 3 and 4. In practice, the source and the spectrophotometer are combined in a common block connected to the probe via a single optic fibre FOER for carrying the incident light as well as for carrying the reflected light.

The light source may comprise upstream a monochromator, whose dispersive principle permits scanning of the spectral field from 400 to 2500 nm.

Determination according to the invention is objective, non-destructive, and is set up on the transformation site in an industrial environment without having recourse to sophisticated, expensive devices. In general, the reliability is improved when numerous spectral data DSP and non-spectral data DAC are integrated in the determination model However, some parameters (1 to 5 for example) of the DAC type (which may vary from one determination model to another according to the piece of meat being analysed, the animal, and the homogeneity of the population) in association with spectral data DSP may suffice to achieve satisfactory reliability.

What is claimed is:

1. A method of determining the quality of meat in a transformation site, comprising:
   a) collecting, on the transformation site, data relating to parameters belonging to the group consisting of breed, age and category of animal and biological and/or physico-chemical parameters of the animal carcass belonging to the group consisting of weight, conformation, fleshing, pH value, colour of the carcass, and thickness of the hide,
   b) obtaining at least one optical spectrum of the meat corresponding to wavelengths belonging to a spectral field ranging from visible light to near infrared, and
   c) combining the data obtained during steps a) and b) with a view to determining the tenderness of the meat according to a predetermined equation relative to a predetermined scale of reference of tenderness.

2. The method according to claim 1, wherein step b) is carried out in reflection and/or transmission mode.

3. The method according to claim 2, wherein step b) comprises:
   b1) providing a probe comprising an emission branch and a reception branch, spaced apart by a predetermined distance;
   b2) inserting the emission and reception branches into a selected piece of meat to a selected depth;
   b3) illuminating the piece of meat by means of the emission branch thus inserted into the piece of meat by wide-band light radiation at a frequency ranging from visible light to near infrared;
   b4) receiving the light transmitted by the piece of meat by means of the receiving branch thus inserted into the piece of meat; and
   b5) recording a transmission spectrum of the piece of meat ranging from visible light to at least near infrared.

4. The method according to claim 1, wherein the equation of determination is drawn up over a series of different pieces of meat of different animals for each of which spectral data and non-spectral data are obtained according to steps a) and b) and compared to a scale of reference drawn up by means of sensorial data and/or data of the shearing force, and/or of the force of compression measured over the significant series of different pieces of meat.

5. The method according to claim 1, wherein the equation of determination is carried out by a multidimensional statistical method in order to obtain a mathematical determination model intended to be used on each piece of meat whose tenderness is to be determined.

6. The method according to claim 1, wherein spectral variables are processed according to an analysis of a main component of a similar process.

7. The method according to claim 1, wherein step b) is carried out on a carcass, quarter, muscle or steak.

8. The method of claim 1, wherein the meat is beef.

9. The method of claim 5, wherein the multidimensional statistical method comprises the method of the smallest partial squares.

10. A device for determining the quality of meat on a transformation site, comprising:
   means of collecting on the transformation site, data relating to parameters belonging to the group consisting of breed, age and category of animal and biological and/or physico-chemical parameters of the animal carcass belonging to the group consisting of weight, conformation, fleshing, pH value, colour of the carcass, and thickness of the hide,
   means of obtaining at least one optical spectrum of the meat corresponding to wavelengths belonging to a spectral field ranging from visible light to near infrared, and
   processing means for combining the data obtained from the means of collecting and means of obtaining with a view to determining the tenderness of the meat according to a predetermined equation relative to a predetermined scale of reference of tenderness.

11. The device according to claim 10, wherein the means of obtaining a spectrum comprises:
   a probe comprising an emission branch and a reception branch, spaced apart a predetermined distance and capable of being inserted into a selected piece of meat to a selected depth;
   a light source capable of sending a wide-band light radiation at a frequency ranging from visible light to near infrared, and optically connected to the emission branch in order to illuminate the piece of meat by means of the emission branch thus inserted into the piece of meat; and measuring means capable of recording a transmission spectrum of the piece of meat ranging from the visible to near infrared and optically connected to the reception branch in order to measure the intensity of the light transmitted by the piece of meat and received by the reception branch thus inserted into the piece of meat.

12. The device according to claim 11, wherein the emission branch comprises a window disposed perpendicular to the longitudinal axis of penetration of the emission branch and at least one emitting optic fibre optically connecting the light source to the window of the first branch.

13. The device according to claim 11, wherein the reception branch comprises a window disposed perpendicular to the longitudinal axis or penetration of the reception branch, opposite the window of the emission branch, and at least one receiving optic fibre optically connecting the window of the second branch to the measuring means.

14. The device according to claim 11, wherein the the two branches is adjustable in order to carry out optical measurements in a volume of meat of a few $cm^3$.

15. The device according to claim 10, wherein the means of obtaining a spectrum comprises:

a probe comprising an emission/reception branch capable of being inserted into a selected piece of meat to a selected depth;

a light source capable of sending a wide-band light radiation at a frequency ranging from the visible to near infrared, and optically connected to the emission/reception branch in order to illuminate the piece of meat by means of the emission/reception branch thus inserted into the piece of meat; and measuring means capable of recording a reflection spectrum of the piece of meat ranging from the visible to near infrared and optically connected to the emission/reception branch in order to measure the intensity of the light reflected by the piece of meat and received by the emission/reception branch thus inserted into the piece of meat.

* * * * *

UNITED STATES PATENT AND TRADEMARK OFFICE
CERTIFICATE OF CORRECTION

PATENT NO. : 6,563,580 B1
DATED : May 13, 2003
INVENTOR(S) : Aignel et al.

It is certified that error appears in the above-identified patent and that said Letters Patent is hereby corrected as shown below:

Title page,
Item [56], References Cited, U.S. PATENT DOCUMENTS, insert
-- 5,668,634    9/1997   Newman........356/445 --

Column 2,
Line 7, after "type of animal", insert -- , --

Column 3,
Line 9, delete "physicochemical", insert -- physico-chemical --

Column 5,
Line 13, delete "nn.", insert -- nm. --

Column 6,
Line 1, after "sirloins of beef", insert -- . --
Line 8, after "or a cross", insert -- , --

Column 7,
Line 26, after "15 cm", insert -- . --

Column 8,
Line 39, delete "advantageous", insert -- advantageously --

Column 9,
Line 40, after "determination model", insert -- . --

Column 11,
Line 18, after "wherein the" insert -- distance between --

Signed and Sealed this

Third Day of May, 2005

JON W. DUDAS
*Director of the United States Patent and Trademark Office*